(12) United States Patent
Yu et al.

(10) Patent No.: US 12,426,814 B2
(45) Date of Patent: Sep. 30, 2025

(54) VITAL-SIGN SENSORS

(71) Applicant: Quanta Computer Inc., Taoyuan (TW)

(72) Inventors: Chih-Hsiung Yu, Taoyuan (TW);
Liang-Chia Huang, Taoyuan (TW);
Chia-Yin Lai, Taoyuan (TW); Bo-Kai Chang, Taoyuan (TW); Wei-Ken Ting, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 573 days.

(21) Appl. No.: 17/931,579

(22) Filed: Sep. 13, 2022

(65) Prior Publication Data

US 2024/0023843 A1    Jan. 25, 2024

(51) Int. Cl.
*A61B 5/1455* (2006.01)
*A61B 5/00* (2006.01)

(52) U.S. Cl.
CPC ........ *A61B 5/14552* (2013.01); *A61B 5/7225* (2013.01); *A61B 2560/0285* (2013.01)

(58) Field of Classification Search
CPC .............. A61B 5/1455; A61B 5/14551; A61B 5/14552; A61B 5/14542; A61B 5/14546; A61B 5/7225
See application file for complete search history.

(56) References Cited

U.S. PATENT DOCUMENTS

| | | | |
|---|---|---|---|
| 5,058,588 A * | 10/1991 | Kaestle | A61B 5/14552 600/323 |
| 5,995,855 A * | 11/1999 | Kiani | A61B 5/14552 600/323 |
| 6,351,658 B1 * | 2/2002 | Middleman | A61B 5/14551 600/323 |
| 7,509,494 B2 * | 3/2009 | Al-Ali | A61B 5/14551 713/168 |
| 11,607,152 B2 | 3/2023 | Moon et al. | |
| 2015/0372433 A1 * | 12/2015 | Lisogurski | A61B 5/14552 439/224 |

FOREIGN PATENT DOCUMENTS

CN    104114089 A    10/2014

OTHER PUBLICATIONS

Chinese language office action dated Aug. 4, 2023, issued in application No. TW 111127027.

\* cited by examiner

*Primary Examiner* — Chu Chuan Liu
(74) *Attorney, Agent, or Firm* — McClure, Qualey & Rodack, LLP

(57) ABSTRACT

A vital-sign sensor is provided. The vital-sign sensor includes an output/input port, a driving/conversion circuit, a detection circuit, and a controller. The output/input port includes a detection pin. The driving/conversion circuit is coupled to the output/input port and controlled by a control signal. The detection circuit includes an input node coupled to the detection pin. The detection circuit generates a detection signal according to a detection voltage at the input node. In response to the output/input port connecting a sensing probe, the detection voltage has a first voltage value, and the controller detects a type of the sensing probe according to the detection signal corresponding to the first voltage value. The controller generates the control signal according to the determined type. The driving/conversion circuit generates a driving signal according to the control signal to drive the sensing probe.

8 Claims, 5 Drawing Sheets

VITAL-SIGN SENSORS

CROSS REFERENCE TO RELATED APPLICATIONS

This Application claims priority of Taiwan Patent Application No. 111127027, filed on Jul. 19, 2022, the entirety of which is incorporated by reference herein.

BACKGROUND OF THE INVENTION

Field of the Invention

The present invention relates to a means of sensing vital signs, and more particularly to a vital-sign sensor which appropriately drives a probe, which is connected to the vital-sign sensor, according to the type of the probe.

Description of the Related Art

Generally, an apparatus for sensing or measuring vital signs includes a host and a probe connected to the host. There are various types of probes that can be selected based on the usage environment and the requirements on the apparatus. For example, probes used in an apparatus for sensing blood oxygen may include disposable probes and reusable probes. The sensing of blood oxygen concentration is accomplished by detecting the light absorption of blood under the skin using a light source and a light sensor in a probe. Since light sources of probes of different types are held at different distances from the skin, the brightness required for the light emitted by the light source to reach the skin is also different. To quickly sense blood oxygen concentration, the light source of a probe has to be driven to emit light at a degree of brightness that is appropriate for the type of probe that is being used.

BRIEF SUMMARY OF THE INVENTION

The present application provides a means of sensing vital signs, and more particularly to a vital-sign sensor, which can appropriately drive a probe connected to the vital-sign sensor according to the type of the probe, such that a value representing the vital sign, for example, a blood oxygen concentration value, can be quickly obtained.

An exemplary embodiment of the present invention provides a vital-sign sensor. The vital-sign sensor comprises an output/input port, a driving/conversion circuit, a detection circuit, and a controller. The output/input port comprises a detection pin. The driving/conversion circuit is coupled to the output/input port and controlled by a control signal. The detection circuit comprises an input node coupled to the detection pin. The detection circuit generates a detection signal according to a detection voltage at the input node. In response to the output/input port connecting a sensing probe, the detection voltage has a first voltage value, and the controller detects a type of the sensing probe according to the detection signal corresponding to the first voltage value. The controller generates the control signal according to the determined type. The driving/conversion circuit generates a driving signal according to the control signal to drive the sensing probe.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated model of carrying out the invention. This description is made for the purpose of illustrating the general principles of the invention and should not be taken in a limiting sense. The scope of the invention is best determined by reference to the appended claims.

Figure 1:
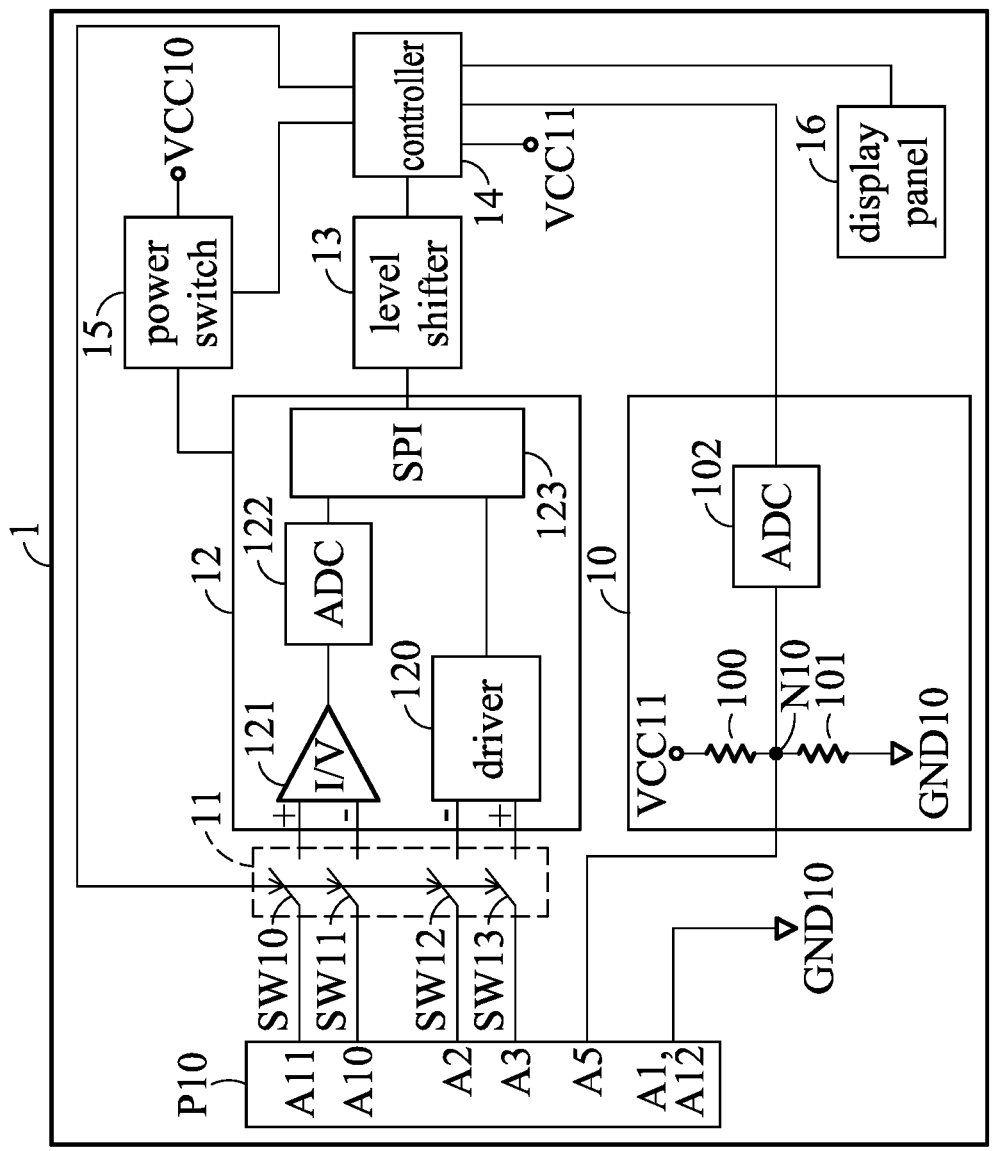
FIG. 1 is a schematic diagram showing a vital-sign sensor according to an embodiment of the present invention.

FIG. 1 shows a vital-sign sensor according to an embodiment of the present invention. A vital-sign sensor 1 shown in FIG. 1 is used to obtain a corresponding value by sensing a vital sign of a to-be-sensed object. In one embodiment, the vital-sign sensor 1 is a blood oxygen sensor, which detects the blood oxygen saturation (SpO2) (a vital sign) of a to-be-sensed object to obtain a blood oxygen concentration value in a percentage. Referring to FIG. 1, the vital-sign sensor 1 comprises an output/input port P10, a detection circuit 10, a switch circuit 11, an analog front end (AFE) circuit 12, a level shifter 13, a controller 14, a power switch 15, and a display panel 16. In an embodiment, the controller 14 may be implemented by a microcontroller unit (MCU).

The output/input port P10 is preferably implemented as a socket for a Universal Serial Bus (USB) interface, and its type is, for example, Type-C. According to the specifications formulated by the USB Implementers Forum (USB-IF), a USB Type-C socket comprises 24 pins A1-A12 and B1-B12, with 12 pins on each side of the socket. Names and definitions of pins of a USB Type-C socket and locations of the pins in the socket are the technical contents that have been published, and detailed descriptions are omitted here. In the following description and the drawings, only the pins related to the technical features of the present application are described and shown. Therefore, it can be understood that the output/input port P10 is implemented as a USB Type-C socket comprises 24 pins A1-A12 and B1-B12. For clarity and simplicity, only the pins A1-A12 are shown in FIG. 1. In drawings of the present application, the configuration locations and sequences of the pins A1-A12 in the output/input port P10 are only provided to explain the technical features of the present application. The actual configuration location and sequence of the pins A1-A12 in the output/input port P10 are based on the USB Type-C specification.

An input node N10 of the detection circuit 10 is coupled to the pin A5 of the output/input port P10, which is the CC1 (Configuration Channel 1) pin defined in the USB Type-C specification. In the embodiment of the present invention, based on the operation of the detection circuit 10, the pin A5 (CC1) is referred to as "detection pin". The detection circuit 10 comprises resistors 100 and 101 and an analog-to-digital converter (ADC) 102. The first terminal of the resistor 100 is coupled to a voltage supply source VCC11, and the second terminal of the resistor 100 is coupled to the input node N10. The first terminal of the resistor 101 is coupled to the input node N10, and the second terminal of the resistor 101 is coupled to a ground terminal GND10. The input terminal of the ADC 102 is coupled to the input node N10, and the output terminal of the ADC 102 is coupled to the controller 14

The power switch 15 is coupled to a voltage supply source VCC10, and the detection circuit 10 and the controller 14 are coupled to the voltage supply source VCC11. When the vital-sign sensor 1 is activated, the voltage supply source VCC10 provides a voltage of, for example, 3.3 volts (V), the voltage supply source VCC11 provides a voltage of, for example, 1.8V, and the voltage of the ground terminal GND10 is 0V.

The switch circuit 11 comprises a plurality of switches SW10-SW13. Each of the switches SW10-SW13 comprises a first terminal and a second terminal. The respective first terminals of the switches SW10-SW13 are coupled to the pins A11 (RXP), A10 (RXN), A2 (TXN), and A3 (TXP) of the output/input port P10 respectively.

The analog front end circuit 12 comprises a driver 120, a current-to-voltage converter (UV) 121, an ADC 122, and a serial peripheral interface (SPI) 123. The input terminal of the driver 120 is coupled to the level shifter 13 through the SPI 123, the negative (−) output terminal thereof is coupled to the second terminal of the switch SW12, and the positive (+) output terminal thereof is coupled to the second terminal of the switch SW13. The negative (−) input terminal of the current-to-voltage converter 121 is coupled to the second terminal of the switch SW11, the positive (+) input terminal thereof is coupled to the second terminal of the switch SW10, and the output terminal thereof is coupled to the input terminal of the ADC 122. The output terminal of the ADC 122 is coupled to the SPI 123. The level shifter 13 is provided between the SPI 123 and the controller 14.

When the vital-sign sensor 1 is activated, the power switch 15 is controlled by the controller 14 to provide the voltage of 3.3V applied from the voltage supply source VCC10 to the analog front end circuit 12, or not to provide the voltage of 3.3V to the analog front end circuit 12.

The detailed operation of the vital-sign sensor 1 will be following paragraphs.

Figure 2:
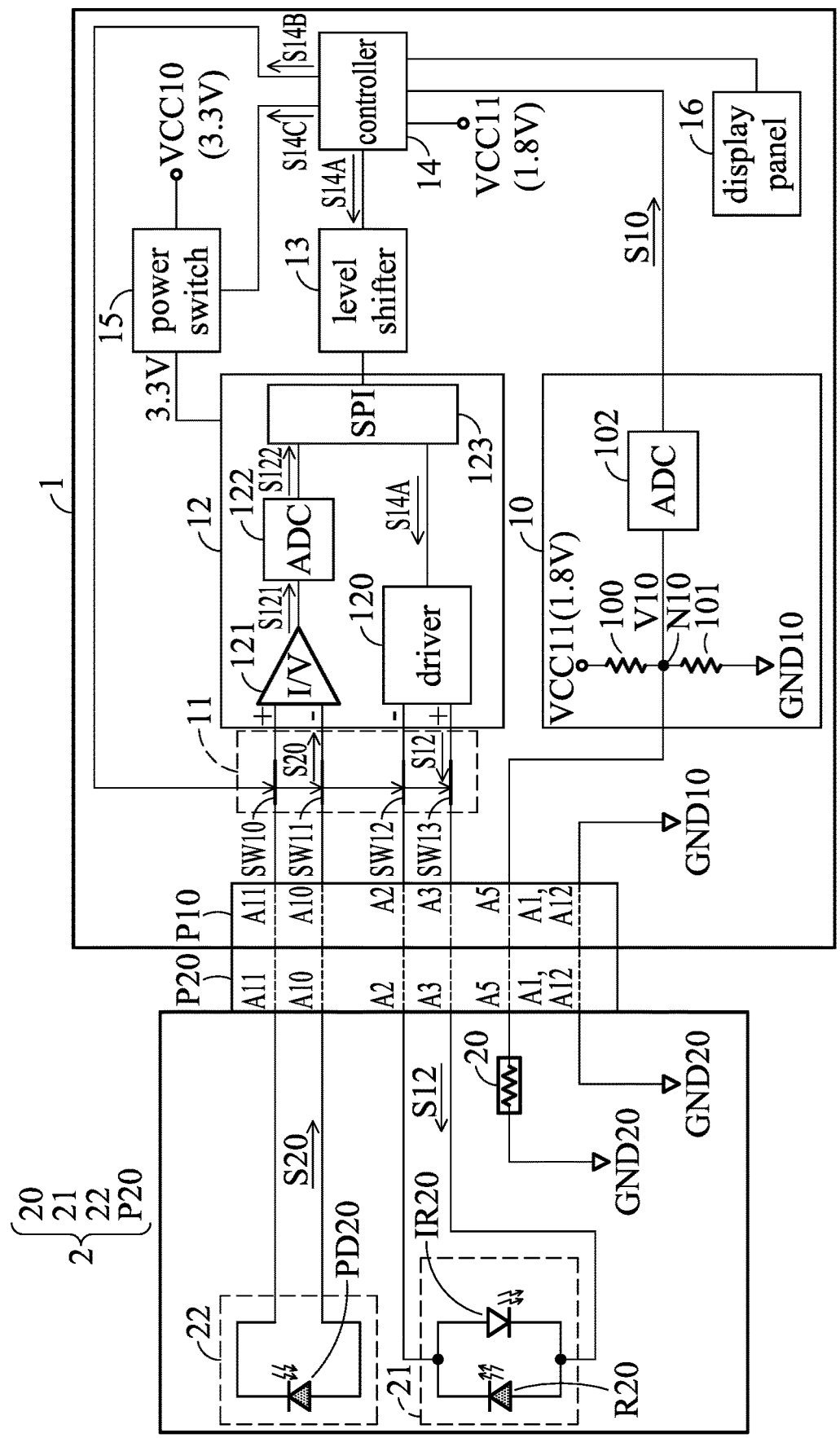
FIG. 2 is a schematic diagram showing the vital-sign sensor of FIG. 1 connected to a sensing probe of a first type according to an embodiment of the present invention.

FIG. 2 is a schematic diagram showing the vital-sign sensor 1 connected to a sensing probe 2 of a first type according to an embodiment of the present invention. Referring to FIG. 2, the sensing probe 2 comprises an output/input port P20, a detection resistor 20, a light emitter 21, and a light sensor 22. The output/input port P20 corresponds to the output/input port P10 of the vital-sign sensor 1, that is, the output/input port P20 is implemented as a USB Type-C plug. The first terminal of the detection resistor 20 is coupled to the pin A5 of the output/input port P20, and the second terminal thereof is coupled to a ground terminal GND20. When the vital-sign sensor 1 is used or operates with the sensing probe 2, the output/input port P20 of the sensing probe 2 is inserted into the output/input port P10 of the vital-sign sensor 1, so that the pins of the output/input port P20 are connected to the corresponding pins of the output/input port P10. In response to the connection, the ground terminal GND20 of the sensing probe 2 and the ground terminal GND10 of the vital-sign sensor 1 are connected to each other. In the embodiment, the type of the sensing probe 2 is a disposable type (the first type), and the resistance value of the detection resistor 20 of the sensing probe 2 is 5.1K ohms (ohm).

In the embodiment, the vital-sign sensor 1 is a blood oxygen sensor to sense the blood oxygen saturation of a to-be-sensed object. The deoxyhemoglobin (Hb) and the oxyhemoglobin (HbO2) in the blood have different absorption capacities for red light (R) and infrared light (IR) having different wavelengths. Therefore, by detecting the absorption of red light (R) and infrared light (IR) by the deoxyhemoglobin (Hb) and the oxyhemoglobin (HbO2) of the blood under the skin of a specific part of the to-be-sensed object (for example, the index finger of the right hand), the sensing of the blood oxygen concentration is achieved. Based on the above-mentioned mechanism for sensing the blood oxygen concentration, the light emitter 21 comprises at least one light emitting diode R20 emitting red light and at least one light emitting diode IR20 emitting infrared light. In FIG. 2, the light emitter 21 comprising one light emitting diode R20 and one light emitting diode IR20 is taken as an example for illustration. The cathode terminal of the light emitting diode R20 and the anode terminal of the light emitting diode IR20 are coupled to the pin A2 of the output/input port P20, and the anode terminal of the light emitting diode R20 and the cathode terminal of the light emitting diode IR20 are coupled to the pin A3 of the output/input port P20. The light sensor 22 comprises a photodiode PD20. The anode terminal and the cathode terminal of the photodiode PD20 are respectively coupled to the pins A10 and A11 of the output/input port P20.

The light emitter 21 is arranged on one side of the sensing probe 2, and the light sensor 22 is arranged on the other side of the sensing probe 2. When the sensing probe 2 clamps or wraps the right index finger of the to-be-sensed object, the light emitted by the light emitting diodes R20 and IR20 passes through the tissue and blood of the right index finger and then collected by the light sensor 22. In the embodiment, the type of the sensing probe 2 is the disposable type (first type). Therefore, when the sensing probe 2 clamps or wraps the right index finger of the to-be-sensed object, the light emitter 21 is closer to the skin of the right index finger.

When the output/input port P20 of the sensing probe 2 is connected to the output/input port P10 of the vital-sign sensor 1 and the vital-sign sensor 1 is used or operates with the sensing probe 2 for sensing blood oxygen (For brevity, in the description of the present application, this situation is referred to as "blood oxygen sensing"), the first terminal of the detection resistor 20 is coupled to the input node N10 of the detection circuit 10 through the pin A5 of the output/input port P20 and the pin A5 of the output/input port P10. Therefore, the detection resistor 20 is connected with the resistor 101 in parallel, and the resistor 100 and the parallel connected resistors 20 and 101 form a voltage divider. The voltage difference between the voltage supply source VCC11 (1.8V) and the ground terminal GND10 is divided by the voltage divider to generate a detection voltage V10 at the input node N10. In the embodiment, the value of the detection voltage V10 is, for example, 0.045V. The ADC 102 converts the detection voltage V10 in an analog form into a digital detection signal S10.

The controller 14 receives the detection signal S10 and obtains the level of the detection voltage V10 according to the detection signal S10. Based on the level of the detection voltage V10, the controller 14 determines that the device connected to the vital-sign sensor 1 is the sensing probe 2 and the type of the sensing probe 2 is the disposable type (first type). According to the determination result of the controller 14, the controller 14 generates a control signal S14A and transmits the control signal S14A to the driver 120 through the level shifter 13 and the SPI 123. In the embodiment, the information carried by the control signal S14A is about the brightness of the light emitting diodes R20 and IR20 in the light emitter 21. Since the type of the sensing probe 2 is the disposable type, the light emitting diodes R20 and IR20 can emit light with low brightness, which is sufficient to achieve the sensing of the blood oxygen concentration. Therefore, the control signal S14A carries the information about low brightness. The driver 120 generates a driving signal S12 according to the control signal S14A. In the embodiment, the driving signal S12 is a differential signal.

Moreover, according to the determination result of the controller 14, the controller 14 further generates switching signals S14B and S14C. The controller 14 transmits the switching signal S14B to the switch circuit 11 to turn on the switches SW10-SW13, so that the negative output terminal and the positive output terminal of the driver 120 are coupled to the pins A2 and A3 of the output/input port P10 through the switches SW12 and SW13 respectively, and the negative input terminal and the positive input terminal of the current-to-voltage converter 121 are coupled to the pins A10 and A11 of the output/input port P10 through the switches SW11 and SW10 respectively. The controller 14 transmits the switching signal S14C to the power switch 15 to control the power switch 15 to supply the received voltage of 3.3V to the analog front end circuit 12 as the voltage required for the analog front end circuit 12 to operate.

The driving signal S12 generated by the driver 120 is transmitted to the light emitter 21 through the turned-on switches SW12-SW13, the pins A2 and A3 of the output/input port P10, and the pins A2 and A3 of the output/input port P20 to drive the light emitting diodes R20 and IR20 to emit red light and infrared light with lower brightness, respectively.

The red and infrared light from the light emitting diodes R20 and IR20 passes through the tissue and blood of the right index finger. The photodiode PD20 senses the remaining red light and infrared light that are not absorbed by the blood and generates a probe output signal S20 corresponding to the amount of red light and the amount of infrared light. In the embodiment, the probe output signal S20 is a current signal, and the current signal includes components corresponding to the amount of red light and the amount of infrared light respectively.

The probe output signal S20 is transmitted to the vital-sign sensor 1 through the pins A10 and A11 of the output/input port P20 and the pins A10 and A11 of the output/input port P10. The current-to-voltage converter 121 receives the probe output signal S20 through the switches SW10 and SW11 and converts the probe output signal S20 from a current signal into a voltage signal S121. The ADC 122 receives the voltage signal S121 and converts the voltage signal S121 in analog form into a digital sensing signal S122. The digital sensing signal S122 is transmitted to the controller 14 through the SPI 123 and the level shifter 13.

Based on the operation of the sensing probe 2, the digital sensing signal S122 represents the blood oxygen saturation (the vital sign) of the to-be-sensed object. The controller 14 receives the digital sensing signal S122 and calculates the blood oxygen concentration value according to the digital sensing signal S122. The controller 14 may transmit the calculated blood oxygen concentration value to the display panel 16, and the display panel 16 shows the blood oxygen concentration value for interpretation by the to-be-sensed subject or health personnel.

Figure 3:
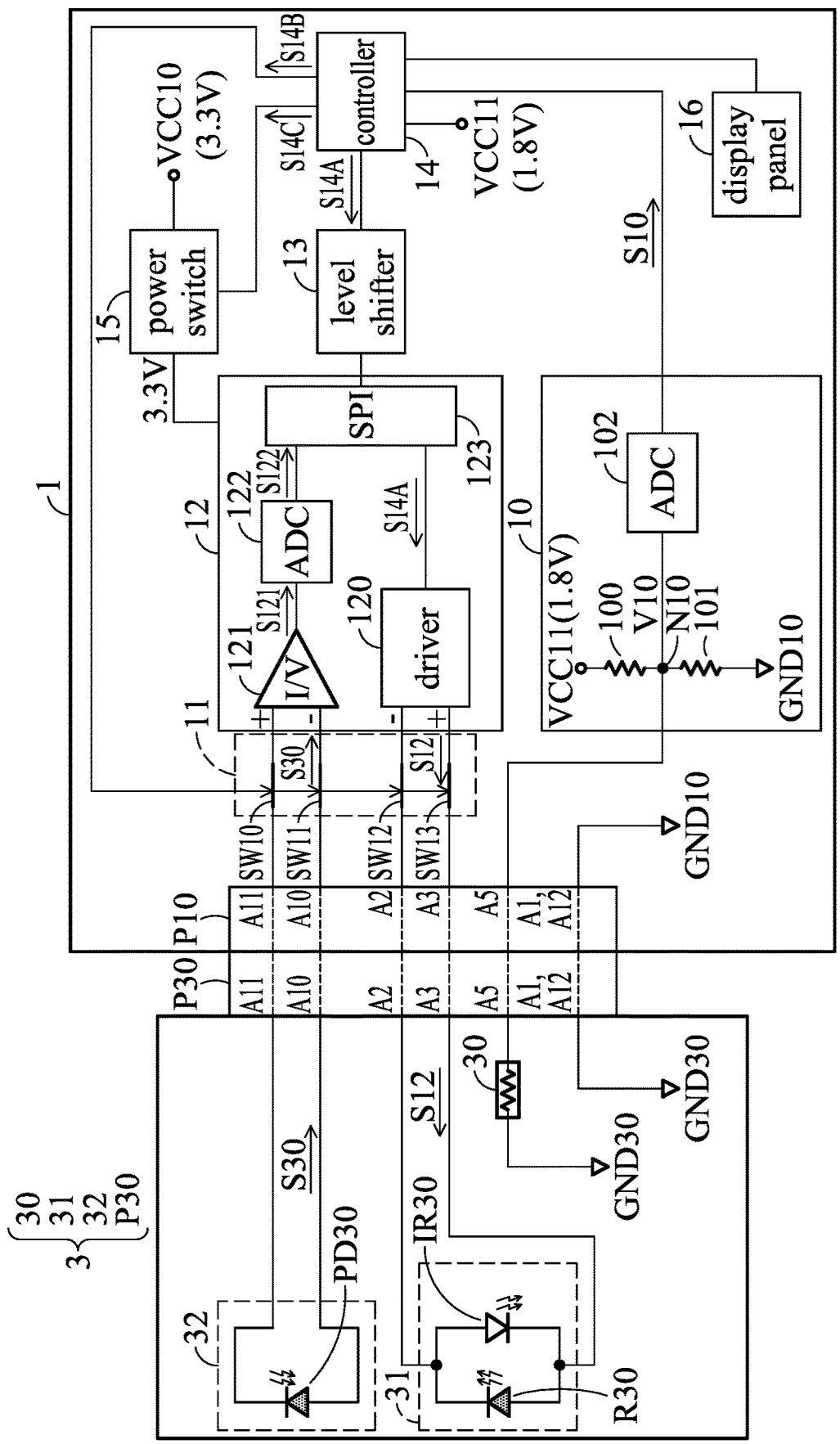
FIG. 3 is a schematic diagram showing the vital-sign sensor of FIG. 1 connected to a sensing probe of a second type according to an embodiment of the present invention.

FIG. 3 is a schematic diagram showing the vital-sign sensor 1 connected to a sensing probe 3 of a second type according to an embodiment of the present invention. Referring to FIG. 3, the sensing probe 3 comprises an output/input port P30, a detection resistor 30, a light emitter 31, and a light sensor 32. The output/input port P30 corresponds to the output/input port P10 of the vital-sign sensor 1, that is, the output/input port P30 is implemented as a USB Type-C plug. The first terminal of the detection resistor 30 is coupled to the pin A5 of the output/input port P30, and the second terminal thereof is coupled to a ground terminal GND30. When the vital-sign sensor 1 is used or operates with the sensing probe 3, the output/input port P30 of the sensing probe 3 is inserted into the output/input port P10 of the vital-sign sensor 1, so that the pins of the output/input port P30 are connected to the corresponding pins of the output/input port P10. In response to the connection, the ground terminal GND30 of the sensing probe 3 and the ground terminal GND10 of the vital-sign sensor I are connected to each other. In the embodiment, the type of the sensing probe 3 is a reusable type (the second type), and the resistance value of the detection resistor 30 of the sensing probe 3 is close to zero ohms. In other embodiments, the sensing probe 3 does not comprise the detection resistor 30, that is, the pin A5 of the output/input port P30 is directly connected to the ground terminal GND30.

The light emitter 31 comprises at least one light emitting diode R30 emitting red light and at least one light emitting diode IR30 emitting infrared light. In FIG. 3, the light emitter 31 comprising one light emitting diode R30 and one light emitting diode IR30 is taken as an example for illustration. The cathode terminal of the light emitting diode R30 and the anode terminal of the light emitting diode IR30 are coupled to the pin A2 of the output/input port P30, and the anode terminal of the light emitting diode R30 and the cathode terminal of the light emitting diode IR30 are coupled to the pin A3 of the output/input port P30. The light sensor 32 comprises a photodiode PD30. The anode terminal and the cathode terminal of the photodiode PD30 are respectively coupled to the pins A10 and A11 of the output/input port P30.

In the embodiment of FIG. 3, the vital-sign sensor 1 and the sensing probe 3 perform operations similar to the operations of the vital-signs sensor 1 and the sensing probe 2 in the embodiment of FIG. 2, and, thus, the related description is omitted here. In the following, only the difference between the embodiment of FIG. 3 and the embodiment of FIG. 2 will be described. In the embodiment, the type of the sensing probe 3 is the reusable type (the second type). Therefore, when the sensing probe 3 clamps or wraps the right index finger of the to-be-sensed object, the light emitter 31 is farther from the skin of the right index finger.

In the embodiment of FIG. 3, the value of the detection voltage V10 is close to or equal to 0V. The ADC 102 converts the detection voltage V10 in the analog form into a digital detection signal S10. The controller 14 obtains the level of the detection voltage V10 according to the detection signal S10 and, based on the level of the detection voltage V10, determines that the device connected to the vital-sign sensor 1 is the sensing probe 3 and the type of the sensing probe 3 is the reusable type (the second type). According to the determination result of the controller 14, the controller 14 generates a control signal S14A. In the embodiment, since the type of the sensing probe 3 is the reusable type, the light emitting diodes R30 and IR30 are required to emit light with a high brightness to achieve the sensing of the blood oxygen concentration. Therefore, the control signal S14A carries the information about high brightness. According to the determination result of the controller 14, the controller 14 further generates switching signals S14B and S14C. The operations of the switch circuit 11 and the power switch 15 performed according to the switching signals S14B and S14C respectively are the same as these recited in the embodiment in FIG. 2, and, thus, the related description is omitted here.

The driving signal S12 generated by the driver 120 is transmitted to the light emitter 31 through the turned-on switches SW12-SW13, the pins A2 and A3 of the output/input port P10, and the pins A2 and A3 of the output/input port P30 to drive the light emitting diodes R30 and IR30 to emit red light and infrared light with higher brightness, respectively. The red and infrared light from the light emitting diodes R30 and IR30 passes through the tissue and blood of the right index finger. The photodiode PD30 senses the remaining red light and infrared light that are not absorbed by the blood and generates a probe output signal S30 corresponding to the amount of red light and the amount of infrared light. In the embodiment, the probe output signal S30 is a current signal, and the current signal includes components corresponding to the amount of red light and the amount of infrared light respectively. The operation of the vital-sign sensor 1 performed based on the probe output signal S30 is the same as that recited in the embodiment in FIG. 2, and, thus, the related description is omitted here.

According to the above embodiments, the analog front end circuit 12 is used to drive the light emitter 21/31 and perform a conversion on the probe output signal S20/S30 from the light sensor 22/32. Therefore, the analog front end circuit 12 is also referred as the driving/conversion circuit.

According to the embodiments of the FIGS. 2 and 3, the vital-sign sensor 1 provided in the present application can determine the type of the sensing probe connected to the vital-sign sensor 1 and drive the light transmitter in the sensing probe according to the determined type to emit light with appropriate brightness corresponding to the determined type. Based on the emitted light with the appropriate brightness, the light sensor of the sensing probe cannot be affected by the distance between the light emitter and the finger, such that the vital-sign sensor 1 can quickly and accurately calculate the blood oxygen concentration value.

Figure 4:
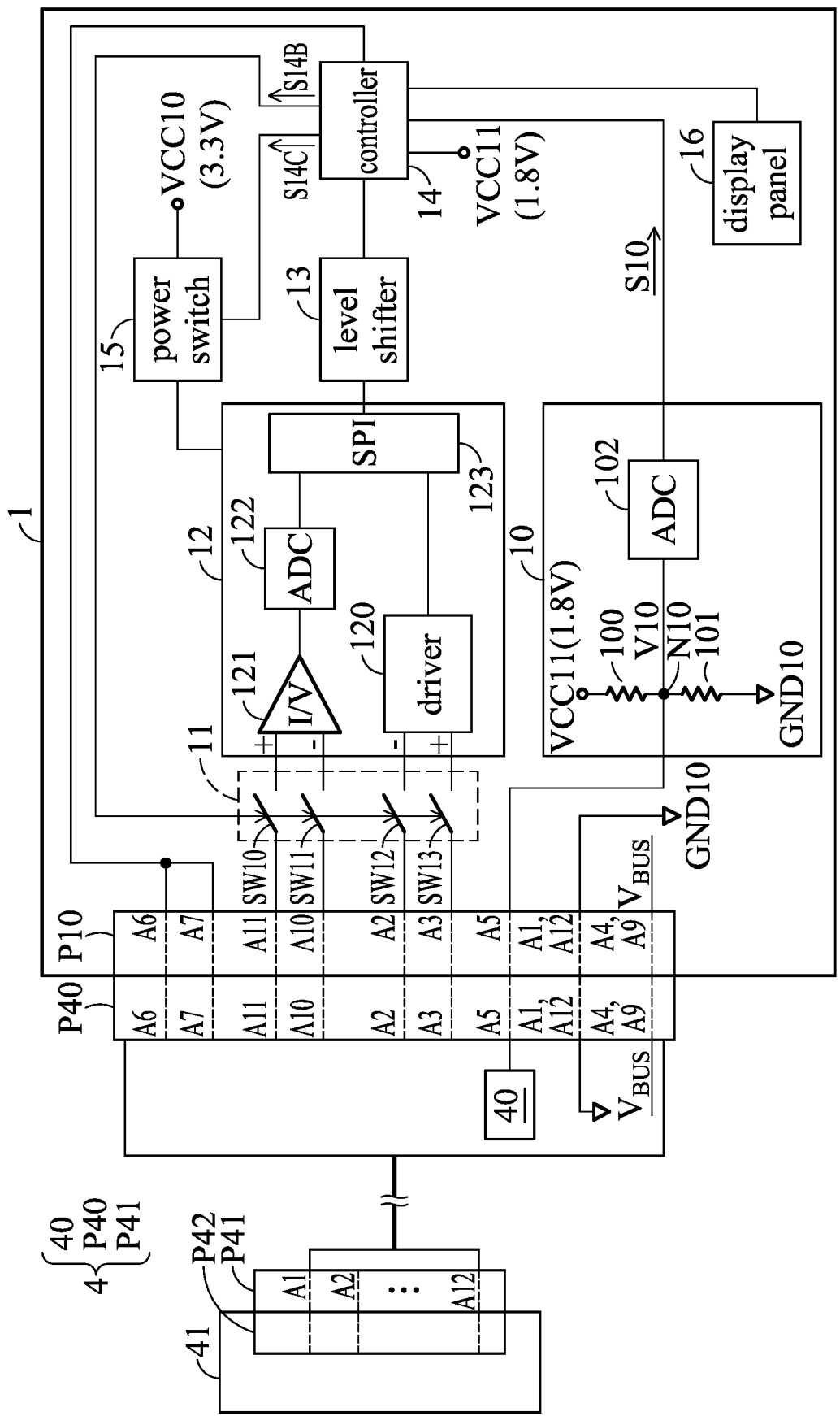
FIG. 4 is a schematic diagram showing the vital-sign sensor of FIG. 1 connected to an external device through a connection line according to an embodiment of the present invention.

FIG. 4 is a schematic diagram showing the vital-sign sensor 1 connected to an external device 41 through a connection line 4 according to an embodiment of the present invention. Referring to FIG. 4, the connection line 4 comprises output/input ports P40 and P41 and a current source 40. In the embodiment, each of the output/input ports P40 and P41 is implemented as a USB Type-C plug. The current source 40 is connected to the pin A5 of the output/input port P40. The external device 41 comprises an output/input port P42, and the output/input port P42 is implemented as a USB Type-C socket. When the vital-sign sensor 1 is used or operates with the external device 41, the output/input port P40 of the connection line 4 is inserted into the output/input port P10 of the vital-sign sensor 1, and the output/input port P41 of the connection line 4 is inserted into the output/input port P42 of the external device 41. In the embodiment shown in FIG. 4, the controller 14 is further coupled to the pins A6 (DP) and A7 (DN) of the output/input port P10.

In FIG. 4, the output/input ports P40-P42 are shown to present the connection between the vital-sign sensor 1, the connection line 4, and the external device 41. The relative size of the output/input ports P40-P42 in FIG. 4 does not represent the actual size. Since the connection between the output/input ports P41 and P42 is a connection between a USB Type-C plug and a USB Type-C socket and the USB Type-C plug-to-socket connection is known to one having ordinary skill in the technical field to which this application belongs, the connection between the pins is not shown in detail.

In the embodiment, the external device 41 may be a computer device. When the connection line 4 is connected to the external device 41 and the vital-sign sensor 1, signals may be transmitted between the external device 41 and the vital-sign sensor 1 through the respective pins A6 and A7 of the output/input ports P40 and P41 of the connection line 4, or the external device 41 may charge the vital-sign sensor 1 through the connection line 4.

In the embodiment, the current source 40 provides a current to the input node N10 through the respective pins A5 of the output/input parts P40 and P10. Based on the input current, the value of the detection voltage V10 at the input node N10 is in the range of 0.47V to 1.63V. The ADC 102 converts the detection voltage V10 in an analog form into a digital detection signal S10. The controller 14 obtains the level of the detection voltage V10 according to the detection signal S10 and determines that the device connected to the vital-sign sensor 1 is not a sensing probe based on the level of the detection voltage V10. In this case, the controller 14 generates a switching signal S14B to turn off the switches SW10-SW13 of the switch circuit 11. Turning off the switches SW10-SW13 can avoid misoperation of the vital-sign sensor 1 by the external device 41. Moreover, the controller 14 also generates a switching signal S14C to control the power switch 15 to stop supplying the voltage of 3.3V to the analog front end circuit 12. Since the device connected to the vital-sign sensor 1 is not a sensing probe, the analog front end circuit 12 does not need to operate. By stopping supplying the voltage of 3.3V to the analog front end circuit 12, power consumption can be reduced. In the embodiment, the controller 14 does not need to generate the control signal S14A for driving any sensing probe.

Figure 5:
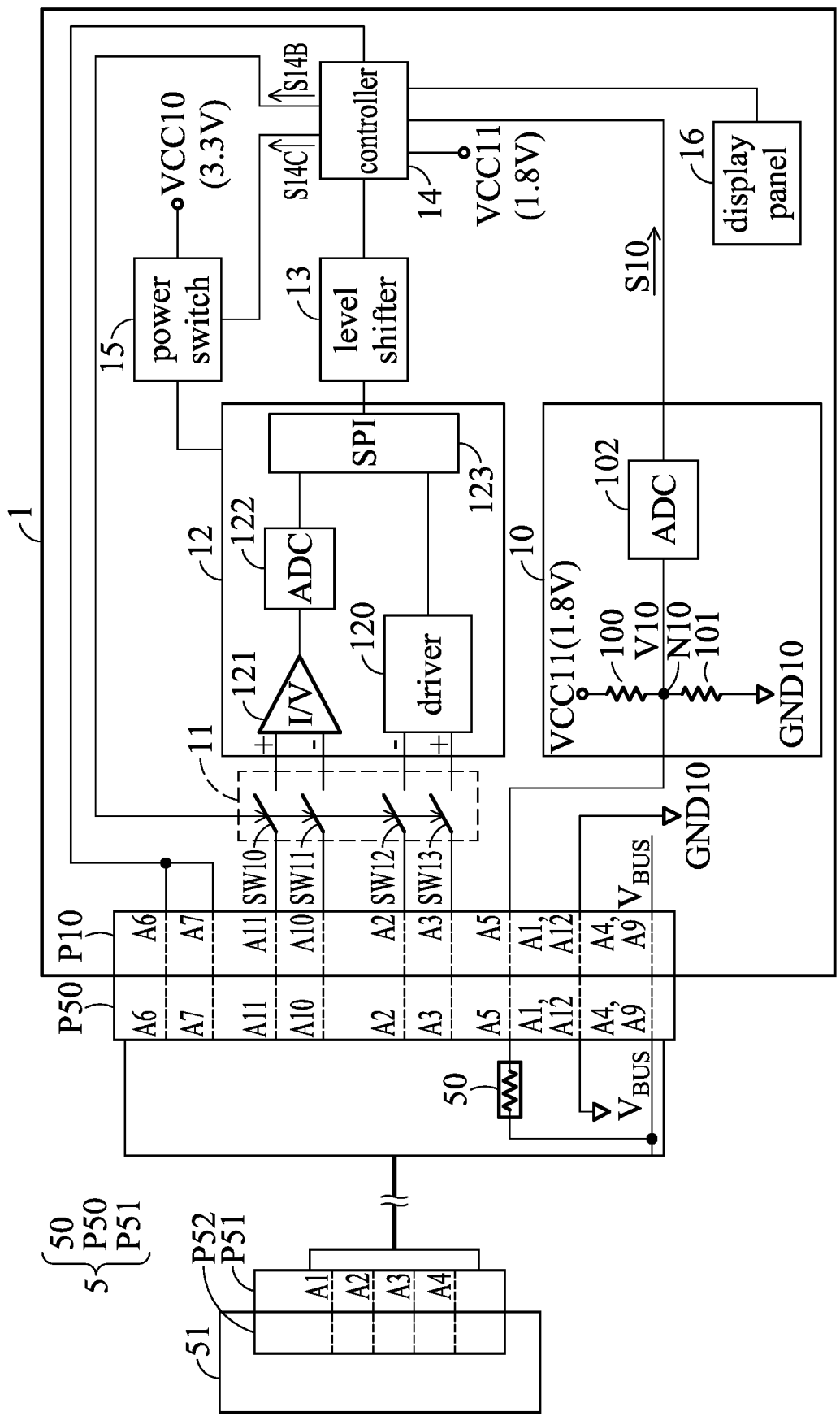
FIG. 5 is a schematic diagram showing the vital-sign sensor of FIG. 1 connected to an external device through a connection line according to another embodiment of the present invention.

FIG. 5 is a schematic diagram showing the vital-sign sensor 1 connected to an external device 51 through a connection line 5 according to an embodiment of the present invention. Referring to FIG. 5, the connection line 5 comprises output/input ports P50 and P51 and a resistor 50. In the embodiment, the output/input port P50 is implemented as a USB Type-C plug, while the output/input port P51 is implemented as a USB Type-A plug. The pins A6 (DP), A7 (DN), A4/A9 ($V_{BUS}$), and A1/A12 (GND) of the output/input port P50 correspond to the pins A3 (D+), A2 (D−), A1 ($V_{BUS}$), and A4 (GND) of the output/input port P51 respectively. The resistor 50 is coupled between the pin A5 of the output/input port P50 and the bus voltage source $V_{BUS}$. The bus voltage source $V_{BUS}$ is connected to the pins A4 and A9 of the output/input port P50. The external device 51 comprises an output/input port P52, and the output/input port P52 is implemented as a USB Type-A socket. When the vital-sign sensor 1 is used or operates with the external device 51, the output/input port P50 of the connection line 5 is inserted into the output/input port P10 of the vital-sign sensor 1, and the output/input port P51 of the connection line 5 is inserted into the output/input port P52 of the external device 51. In the embodiment shown in FIG. 5, the controller 14 is further coupled to the pins A6 and A7 of the output/input port P10.

In FIG. 5, the output/input ports P50-P52 are shown to present the connection between the vital-sign sensor 1, the connection line 5, and the external device 51. The relative size of the output/input ports P50-P52 in FIG. 5 does not represent the actual size. Since the connection between the output/input ports P51 and P52 is a connection between a USB Type-A plug and a USB Type-A socket and the USB Type-A plug-to-socket connection is known to one having ordinary skill in the technical field to which this application belongs, the connection between the pins is not shown in detail.

In the embodiment, the external device 51 may be a computer device. When the connection line 5 is connected to the external device 51 and the vital-sign sensor 1, signals may be transmitted between the external device 51 and the vital-sign sensor 1 through the pins A6 and A7 of the output/input port P50 of the connection line 5 and the pins A3 and A2 of the output/input port P51 of the connection line 5, or the external device 51 may charge the vital-sign sensor 1 through the connection line 5.

In the embodiment, the resistor 100 and the parallel connected resistors 50 and 101 form a voltage divider, and the value of the detection voltage V10 at the input node N10 is 0.47V. The ADC 102 converts the detection voltage V10 in an analog form into a digital detection signal S10. The controller 14 obtains the level of the detection voltage V10 according to the detection signal S10 and determines that the device connected to the vital-sign sensor 1 is not a sensing probe based on the level of the detection voltage V10. In this case, the controller 14 generates a switching signal S14B to turn off the switches SW10-SW13 of the switch circuit 11. Turning off the switches SW10-SW13 can avoid misoperation of the vital-sign sensor 1 by the external device 51. Moreover, the controller 14 also generates a switching signal S14C to control the power switch 15 to stop supplying the voltage of 3.3V to the analog front end circuit 12. Since the device connected to the vital-sign sensor 1 is not a sensing probe, the analog front end circuit 12 does not need to operate. By stopping supplying the voltage of 3.3V to the analog front end circuit 12, power consumption can be reduced. In the embodiment, the controller 14 does not need to generate the control signal S14A for driving any sensing probe.

According to the embodiments of FIGS. 4 and 5, when the vital-sign sensor 1 is not connected to the sensing probe, but is connected to other external devices, through controlling the switch circuit 11 and the power switch 15 by the controller 14, misoperation of the vital-sign sensor 1 by the external device 51 can be avoided, and power consumption can be reduced.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A vital-sign sensor comprising:
   an output/input port comprising a detection pin;
   a driving/conversion circuit, coupled to the output/input port, controlled by a control signal;
   a detection circuit comprising an input node coupled to the detection pin and generating a detection signal according to a detection voltage at the input node;
   a controller, coupled to the detection circuit, receiving the detection signal; and
   a switch circuit disposed between the output/input port and the driving/conversion circuit and controlled by a switching signal,
   wherein in response to the output/input port connecting a sensing probe, the detection voltage has a first voltage value, and the controller detects a type of the sensing probe according to the detection signal corresponding to the first voltage value;
   wherein the controller generates the control signal according to the determined type, and the driving/conversion circuit generates a driving signal according to the control signal to drive the sensing probe;
   wherein in response to the detection voltage having the first voltage value, the controller generates the switching signal according to the detection signal corresponding to the first voltage value to turn on the switch circuit; and
   wherein in response to the output/input port connected to no device or connected to a device other than the sensing probe, the defection voltage has a second voltage value, and the controller generates the switching signal according to the detection signal corresponding to the second voltage value to turn off the switch circuit.

2. The vital-sign sensor as claimed in claim 1,
   wherein in response to the output/input port connecting the sensing probe, the driving/conversion circuit receives a probe output signal from the sensing probe and generates a digital sensing signal according to the probe output signal, and
   wherein the controller receives the digital sensing signal and generates a value representing a vital sign according to the digital sensing signal.

3. The vital-sign sensor as claimed in claim 2, wherein the vital sign is a blood oxygen saturation, and the value is a blood oxygen concentration value.

4. The vital-sign sensor as claimed in claim 1, wherein the type of the sensing probe is a disposable type or a reusable type.

5. The vital-sign sensor as claimed in claim 4, wherein in response to the output/input port connecting the sensing probe, the sensing probe provides a detection resistance value to the detection pin, and the first voltage value of the detection voltage is determined by the detection resistance value.

6. The vital-sign sensor as claimed in claim 1,
   wherein the sensing probe comprises a light emitter, and the driving signal is configured to control the light emitter, and
   wherein in response to the controller changing the control signal according to the determined type, the driving/conversion circuit changes brightness of the light emitter through the driving signal.

7. The vital-sign sensor as claimed in claim 1, wherein the detection circuit comprises:
   a first resistor having a first terminal coupled to a first voltage supply source and a second terminal coupled to the input node;
   a second resistor having a first terminal coupled to the input node and a second terminal coupled to a ground terminal; and
   an analog-to-digital converter, coupled to the input node, converting the detection voltage into the detection signal.

8. The vital-sign sensor as claimed in claim 1, wherein the vital-sign sensor is a blood oxygen sensor.

* * * * *